United States Patent
Bainton et al.

(10) Patent No.: US 10,245,376 B2
(45) Date of Patent: Apr. 2, 2019

(54) ASSEMBLY INCLUDING A NEEDLE FOR ADMINISTERING A FLUID

(71) Applicant: Sanofi, Paris (FR)

(72) Inventors: Michael Bainton, Kineton (GB); Matthew Jones, Warwick (GB)

(73) Assignee: Sanofi, Paris (FR)

(*) Notice: Subject to any disclaimer, the term of this patent is extended or adjusted under 35 U.S.C. 154(b) by 81 days.

(21) Appl. No.: 15/115,982

(22) PCT Filed: Feb. 2, 2015

(86) PCT No.: PCT/EP2015/052036
§ 371 (c)(1),
(2) Date: Aug. 2, 2016

(87) PCT Pub. No.: WO2015/117913
PCT Pub. Date: Aug. 13, 2015

(65) Prior Publication Data
US 2017/0165418 A1 Jun. 15, 2017

(30) Foreign Application Priority Data

Feb. 5, 2014 (EP) ..................... 14305159

(51) Int. Cl.
*A61M 5/158* (2006.01)
*A61M 5/32* (2006.01)
(Continued)

(52) U.S. Cl.
CPC .............. *A61M 5/158* (2013.01); *A61M 5/14* (2013.01); *A61M 5/1407* (2013.01);
(Continued)

(58) Field of Classification Search
CPC ........ A61M 5/158; A61M 5/14; A61M 5/142; A61M 5/14244; A61M 5/14248;
(Continued)

(56) References Cited

U.S. PATENT DOCUMENTS

| 9,119,939 B2* | 9/2015 | Botich | A61M 25/0631 |
| 2001/0025168 A1* | 9/2001 | Gross | A61M 5/14248 |
| | | | 604/506 |

(Continued)

FOREIGN PATENT DOCUMENTS

| EP | 1495775 | 1/2005 |
| JP | 2002-505601 | 2/2002 |
| WO | WO 98/57683 | 12/1998 |

OTHER PUBLICATIONS

International Search Report and Written Opinion in International Application No. PCT/EP2015/052036, dated Apr. 8, 2015, 10 pages.
(Continued)

*Primary Examiner* — Bhisma Mehta
*Assistant Examiner* — James D Ponton
(74) *Attorney, Agent, or Firm* — Fish & Richardson P.C.

(57) ABSTRACT

An assembly including a needle (3) for administering a fluid is presented. The needle (3) comprises a hollow needle body (4) to guide the fluid. The needle body (4) is furthermore formed such that an inlet section (20) of the needle body (4) defines a first flow direction for the fluid and an outlet section (21) of the needle body (4) defines a second flow direction for the fluid, wherein the first flow direction is inclined with respect to the second flow direction.

14 Claims, 4 Drawing Sheets

(51) Int. Cl.
   *A61M 5/20*   (2006.01)
   *A61M 5/14*   (2006.01)
   *A61M 5/178*  (2006.01)
   *A61M 5/142*  (2006.01)
   *A61M 5/315*  (2006.01)
   *A61M 5/34*   (2006.01)

(52) U.S. Cl.
   CPC .............. *A61M 5/178* (2013.01); *A61M 5/20* (2013.01); *A61M 5/32* (2013.01); *A61M 5/329* (2013.01); *A61M 5/3216* (2013.01); *A61M 5/3155* (2013.01); *A61M 2005/1402* (2013.01); *A61M 2005/14252* (2013.01); *A61M 2005/14256* (2013.01); *A61M 2005/1581* (2013.01); *A61M 2005/2026* (2013.01); *A61M 2005/3206* (2013.01); *A61M 2005/341* (2013.01)

(58) Field of Classification Search
   CPC ........... A61M 2005/1402; A61M 2005/14252; A61M 5/32; A61M 5/3202; A61M 5/3205; A61M 5/321; A61M 2005/3208; A61M 2005/1581; A61M 5/31533; A61M 5/31545; A61M 5/31546; A61M 5/31548; A61M 5/3155; A61M 5/31551; A61M 5/31553; A61M 5/31555
   See application file for complete search history.

(56) References Cited

U.S. PATENT DOCUMENTS

| | | | |
|---|---|---|---|
| 2005/0090781 A1* | 4/2005 | Baba ................. | G06F 19/00 604/209 |
| 2005/0197650 A1* | 9/2005 | Sugimoto ............... | A61M 5/20 604/890.1 |
| 2007/0219480 A1* | 9/2007 | Kamen ................ | G05D 7/0647 604/20 |
| 2013/0296785 A1* | 11/2013 | Cabiri ............... | A61M 5/14248 604/151 |

OTHER PUBLICATIONS

International Preliminary Report on Patentability in International Application No. PCT/EP2015/052036, dated Aug. 9, 2016, 8 pages.

\* cited by examiner

ASSEMBLY INCLUDING A NEEDLE FOR ADMINISTERING A FLUID

CROSS-REFERENCE TO RELATED APPLICATIONS

This application is a U.S. national stage application under 35 USC § 371 of International Application No. PCT/EP2015/052036, filed on Feb. 2, 2015, which claims priority to European Patent Application No. 14305159.7, filed on Feb. 5, 2014, the entire contents of which are incorporated herein by reference.

The present disclosure relates to a needle for administering a fluid, a needle unit, an assembly and a drug delivery device, such as an injector-type device.

Certain implementations of the present disclosure can provide an improved needle and an according needle unit and assembly, whereby an improved administration or delivery device such as a drug delivery device can be provided.

Such implementations are achieved by the subject-matter of the independent claim. Advantageous embodiments and refinements are subject-matter of the dependent claims.

One aspect of the present disclosure relates to a needle for administering a fluid, the needle comprising a hollow needle body to guide the fluid. The needle body may comprise a single component only. The needle body may e.g. be a tube. Alternatively, the needle body may comprise more than one, e.g. two, components. The needle body is formed such that an inlet section of the needle body defines a first flow direction for the fluid. Preferably, the inlet defines a section of the needle body which is suitable to receive the fluid or let the fluid into the needle body. The needle body further comprises an outlet section which defines a second flow direction for the fluid, wherein the first flow direction is inclined with respect to the second flow direction. As compared to the inlet section, the outlet section is, preferably, a section of the needle body which is intended or suitable such that fluid, which has previously been received by the needle body, can be ejected from said needle body via the outlet section in order to administer the fluid.

In an embodiment, the inlet section, as well as the outlet section define end sections of the needle body.

In an embodiment, the inlet section and/or the outlet section are not curved such that said sections each define a straight flow direction, i.e. the first flow direction and the second flow direction, respectively.

As an advantage, the needle may be used or applied in administering or injection devices, such as drug delivery devices with alternative geometries. Such geometries may ease or aid a user in using or operating said devices. For instance, the inlet section may be aligned to a longitudinal axis of the device, while the outlet section is inclined with respect to the longitudinal axis. In this way, the fluid path may be redirected according to the specific requirement of the respective device. For example, the first flow direction may be aligned parallel to a surface into which the fluid is to be administered or dispensed, e.g. the skin of a patient or the user. Then, the fluid may be redirected to the second flow direction, e.g. a direction parallel to the normal of the surface.

Particularly, an operation of the drug delivery device can be rendered more controllable and users with limited manual dexterity may be aided in operating the device.

In an embodiment, the needle body is formed such that the first flow direction and the second flow direction are right-angled or perpendicular. According to this embodiment, the needle may be applied in a device, wherein fluid may be conveyed through the needle from, e.g. a cartridge to an element or the surface via a right angle. Such a geometry may be advantageous with respect to the usability or controllability of the administering or dispensing process. Particularly, the device may then be embodied such that the surface into which the fluid is to be administered has to laterally contact a body or housing of the device while the first flow direction is still aligned parallel to said surface.

In an embodiment, the needle body comprises a bend which preferably immediately connects the inlet section and the outlet section. The needle body may be a single tube with an integral bend, or the inlet section and outlet section may be formed by separate needle body parts or tubes connected by a third part that comprises or exhibits the bend. The provision of the bend expediently allows the first flow direction and the second flow direction to be inclined. The bend may further be an arc. Preferably, the bend extends over a single plane only. Preferably, the bend furthermore extends over an angle of less than 270°, preferably less than 180°, most preferably less than 120° such that the needle body is, preferably, not wound over one or more turns or windings.

In an embodiment, the needle body defines a plane or has a planar configuration such that it extends over a single plane only. In other words, the needle or the needle body is configured to redirect the flow of fluid only over the mentioned single bend in the plane. In the following, the terms "needle" or "needle body" may be used interchangeable or synonymously.

A further aspect relates to a needle unit comprising the needle, the needle being fixed to a needle hub and a needle housing which covers or houses a part of the bend of the needle body. Preferably, the needle unit is configured such that it can be pressed or fixed to the housing without being screwed. As an advantage of the needle housing, the bend of the needle body or the needle itself may be supported or protected against external influences. Furthermore, the needle housing may guide or stabilize the needle body. A further advantage of the needle housing relates to an optical or visual shielding of the needle, wherein the needle housing prevents or hinders a user of the needle unit or the device from viewing the needle. A visible needle may, in turn, cause difficulty for needle-phobic patients or users of the device. Additionally, the needle and/or the needle hub may be manipulated by the user via the needle housing. Preferably, the needle, the needle hub and/or the needle unit can be rotated with respect to the housing by rotation or manipulation of the needle housing.

A further aspect relates to an assembly comprising the needle or the needle unit, and a reservoir retaining a fluid, wherein the needle is fluidly connected to the reservoir and a housing, wherein the needle or the needle unit is mounted, preferably rotatably mounted, to the housing.

A further aspect relates to a drug delivery device comprising the assembly. The housing may be or relate to a housing of the drug delivery device.

The needle, the needle unit and the assembly, preferably, relate to drug delivery devices that can be operated to deliver a number of user variable doses of medicament from a cartridge via a needle. Preferably, the assembly relates to a semiautomatic or an automatically driven drug delivery device.

In an embodiment, the assembly is configured such that the needle hub is axially secured but rotatable with respect to the housing. According to this embodiment, the needle unit and/or the needle hub are, preferably, fixed to the housing by any suitable means but, preferably, without being screwed to the housing. Possibly, the device length can also be kept small and/or the device concept can be further simplified in this way In an embodiment, the needle hub is rotatable around a longitudinal axis of the housing and wherein the first flow direction is aligned parallel to the longitudinal axis of the housing. Particularly, the needle hub may be rotatable around the first flow direction. According to this embodiment, the needle body can, advantageously, be made accessible for an administration or hidden or deactivated e.g. during storage by a rotation of the needle hub.

In an embodiment, the housing comprises a first housing part and a second housing part. The needle is secured to the first housing part. The assembly further comprises a drive mechanism. The assembly is configured such that the first housing part is movable, relative to the second housing part to activate the drive mechanism, whereby fluid can be administered or dispensed through the needle.

As an advantage, the fluid may be administered by the user just by relatively moving the first and the second housing part. Thereby, usability as well as controllability of the administration is significantly eased as, particularly users with limited manual dexterity, only have to move said housing parts with respect to each other. This is particularly advantageous, as the housing parts are usually easy to grip, easy to identify as well as accessible to the user.

In an embodiment, the first housing part and the second housing part are pivotally connected to each other. This allows a relative movement between the first and the second housing part without requiring said housing parts to be entirely disconnected from each other. Preferably, the first housing part and the second housing part are pivotally connected to each other at a proximal end of the housing. With this arrangement, as the needle enters the skin, the tip of the needle may move slightly axially, e.g. in the proximal direction, which may cause discomfort to the patient. To prevent this, the outlet section of the needle may be curved, with a radius of curvature centred on the pivot point between the first housing part and the second housing part.

In an embodiment, the outlet section of the needle is curved with a radius of curvature centred on the pivot point between the first housing part and the second housing part.

In an alternative embodiment, the first housing part and second housing part are arranged and configured such that the housing parts slide relative to each other along the axis of the outlet section of the needle to activate the drive mechanism.

In an embodiment, a first housing part is spring-biased away from the second housing part or vice versa. According to this embodiment, a first, open or ready-to-dispense state of the assembly or the device may be defined, wherein the first and the second housing part are already separated, such that they may be moved with respect to each other, e.g. during a dispensing operation. Thereby, the assembly may be switched to a second state or closed state.

A biasing mechanism or element, e.g. comprising a biasing spring is, expediently, provided at or near a distal end of the housing.

In an embodiment, the second housing part comprises an opening. The assembly is, furthermore, configured such that by a movement of the first housing part with respect to the second housing part, the needle is at least partly movable through the opening such that the outlet section of the needle body protrudes through the opening from the housing. According to this embodiment, the assembly or the device may be prepared for an administration or dispensing operation as the needle, or as the case may be, the outlet section of the needle body, is made accessible to a surface or an element to or into which the fluid is to be administered.

In an embodiment, the first housing part retains the drive mechanism. The assembly is, furthermore, configured such that, as soon and preferably only if, the outlet section protrudes a certain distance through the opening during movement of the first housing part with respect to the second housing part, fluid is administered through the needle.

Thereby, it is advantageously achieved that by the relative movement of the first and the second housing part, the device or the assembly can sequentially be prepared for an administration operation and then, the fluid can finally be administered through the needle.

In an embodiment, the second housing part comprises a contact area for contacting the surface into which the fluid is to be administered. The opening is, furthermore, provided in a region of the contact area. According to this embodiment, the previously mentioned functionality is achieved most expediently.

In an embodiment, the needle is rotatable from an administration position to a storage position, and wherein the assembly is configured such that when the needle is in the storage position, the needle is prevented from being visible for the user. Preferably, in this embodiment, the second flow direction is aligned parallel to a plane defined by the contact area. Generally, the needle hub being arranged in the storage position provides the advantage that the user is not confused and/or irritated by the sight of the needle in case that he suffers from needle phobia, for instance.

In an embodiment, the second housing part comprises a shield being arranged to prevent or hinder the outlet section of the needle from being visible for the user. Thereby, it is achieved that, even during an operation, as for example an administration operation of the assembly or the device, the usability is eased or rendered more comfortable, as the needle may not completely be visible for the user during the whole administration operation.

In an embodiment, the drug delivery device comprises a priming mechanism in addition to the drive mechanism, wherein the priming mechanism is configured such that one or more priming doses of fluid can be administered by activating the priming mechanism. Preferably, the priming mechanism is configured such that it can be activated only when the assembly or the device is in a closed or second state, i.e. when the first housing part has already been moved with respect to the second housing part such that said housing parts abut each other against the mentioned spring-biasing.

In an embodiment, the needle is an injection needle for injecting the fluid.

In an embodiment, the fluid is a drug or medicinal product.

In an embodiment, the drug delivery device is a semiautomatic injector or an injector which is automatically driven, e.g. by a motor or drive spring. According to this embodiment, the force necessary for the administration has, advantageously, not to be expended by the user. Consequently, said force has, advantageously, also not to be counteracted by the surface to or into which the fluid is to be administered.

The term "fluid", "drug" or "medicinal product", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by Δ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous aspects of the subject matter of the disclosure will become apparent from the following description of the exemplary embodiment in conjunction with the figures, in which.

Like elements, elements of the same kind and identically acting elements may be provided with the same reference numerals in the figures. Additionally, the figures may be not true to scale.

Rather, certain features may be depicted in an exaggerated fashion for better illustration of important principles.

Figure 1A:
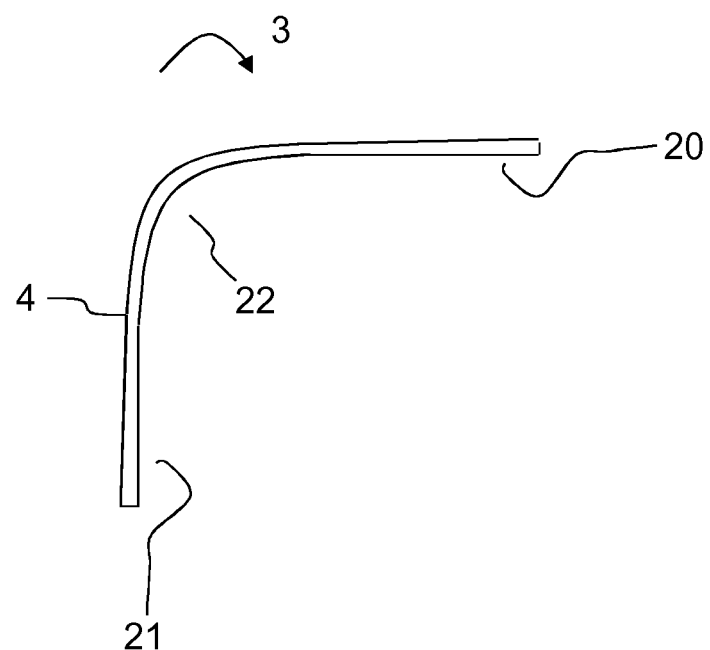
FIG. 1A shows a schematic view of a needle.

FIG. 1A shows a needle 3. The needle 3 comprises or consists of a needle body 4. The needle body 4 comprises an inlet section 20 and an outlet section 21. The needle body 4 further comprises a bend 22 or bend section between the inlet section 20 and the outlet section 21. The bend 22 connects the inlet section 20 and the outlet section 21. The needle body 4 may comprise a single component only (as shown in FIG. 1A). The needle body 4 may e.g. be a tube. The needle body 4 may be a single tube with an integral bend 22, for example. Alternatively, the needle body 4 may—although this is not explicitly indicated in the figures—comprise more than one, e.g. two, components, wherein the inlet section 20 and outlet section 21 may be separate tubes connected by a third part that comprises the bend 22. The inlet section defines a first flow direction and the outlet section defines a second flow direction for the fluid which is to be administered through the needle 3. The first and the second flow direction, preferably, run linearly. The first flow direction is, preferably, an inlet flow direction determining the direction of fluid which is entering the needle body 4 via the inlet section 20. The second flow direction is, preferably, an outlet flow direction determining the direction of fluid which is exiting the needle body 4 via the outlet section 21. In FIG. 1A, the needle body 4 is formed such that the first flow direction and the second flow direction are right-angled, as the inlet section 20 is right-angled with respect to the outlet section 21. Alternatively, the bend 22 could be configured such that the bend 22 defines an angle different from 90°. Preferably, the bend 22 only extends over a single plane, only, such that the needle body 4 defines or runs in said plane. Preferably, the bend extends over an angle of less than 270°, preferably less than 180°, most preferably less than 120°.

Figure 1B:
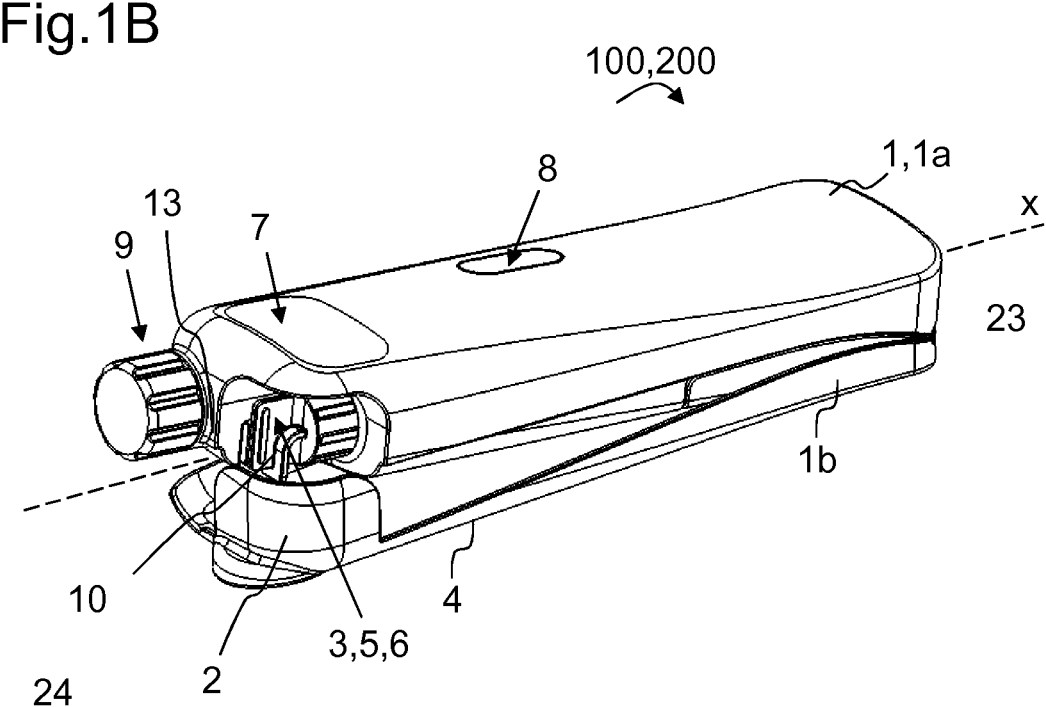
FIG. 1B shows a perspective view of an assembly in a first state.
Figure 1C:
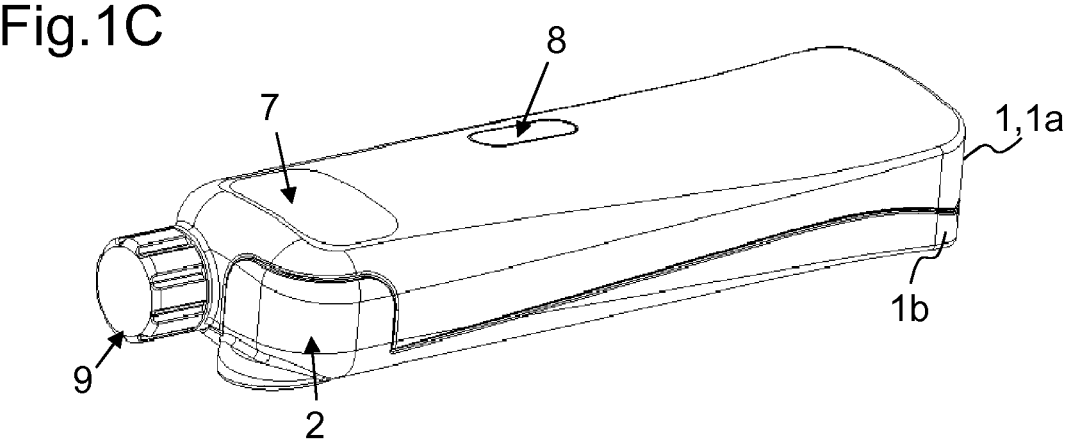
FIG. 1C shows a perspective view of the assembly in a second state.

FIG. 1B shows an assembly 100 and/or a drug delivery device 200. The drug delivery device 200 may relate to all parts shown in FIG. 1 including all inner components, while the assembly 100 may only pertain to several of the depicted parts. The drug delivery device 200 comprises the assembly 100. The assembly 100 comprises a housing 1. The housing 1, preferably also constitutes a housing of the drug delivery device 200.

The housing 1 comprises a first housing part 1a. The housing 1 further comprises a second housing part 1b. The first housing part 1a and the second housing part 1b are movable with respect to each other. The assembly 100 comprises a proximal end 23 and a distal end 24, wherein the proximal end 23 is e.g. spaced from the distal end 24 along a longitudinal axis X of the housing 1.

The first and the second housing part 1a, 1b are pivotally connected to each other at the proximal end 23, e.g. by means of a hinge (not explicitly indicated). The outlet section 21 of the needle 3 may be curved (embodiment not explicitly shown), with a radius of curvature centred on the pivot point between the first housing part 1a and the second housing part 1b. Alternatively, the first housing part 1a and second housing part 1b may slide relative to each other along the axis of the outlet section 21 of the needle 3.

Furthermore, the first housing part 1a is spring-biased away from the second housing part 1b or vice versa. The spring-biasing is, e.g. effected via a biasing spring (not explicitly indicated), preferably at or near the distal end 24 of the device 200. The biasing spring may tend to separate or urge the first and the second housing part 1a, 1b away from each other. The separation of the first and the second housing part 1a, 1b is, expediently counteracted by a stop (not explicitly indicated).

By the biasing and the stop, a first, open or ready-to-dispense state of the assembly 100, as depicted in FIG. 1B can be defined such that in said state, the first housing part 1a may be moved with respect to the second housing part 1b against the resilience of the biasing. In other words, the housing 1, the assembly 100 or the device 200 may be closed. Said movement or closing relates to an administration or delivery operation of fluid. Therefore, the first housing part 1a may be pressed at its distal end 24 towards and relative to the second housing part 1b, for example.

The first housing part 1a is further provided with a needle unit 5. The needle unit 5 is, fixedly connected with, preferably pressed or snapped on the first housing part 1a. Preferably, the needle unit 5 is configured such that it can be pressed or fixed to the first housing part 1a without being screwed to the first housing part 1a. The needle unit 5 comprises the needle 3 (cf. FIG. 10). The needle unit 5 further comprises a needle hub 6. The needle 3 is fixed to the needle hub 6. The needle hub 6 is, preferably, fixedly connected to the needle body 4. The needle hub 6 may retain or bear the needle body 4. The needle unit 5 further comprises a needle housing 10. The needle housing 10 is, preferably, integrally formed with the needle hub 6. Alternatively, the needle housing 10 and the needle hub 6 may be separate components. The needle housing 10 covers a part of the bend 22 of the needle body 4. In FIG. 1B the needle body 4 is covered by the needle housing 10. Since the needle housing 10 also covers the bend 22 of the needle body 4, the needle housing is also bent.

The needle hub 6 and with it the needle 3 is axially secured but rotatable with respect to the housing 1 around the longitudinal axis X of the housing 1 and/or around the first flow direction.

In one embodiment, the second housing part 1b may be opened or separated further from the first housing part 1a in the ready-to-dispense state, to provide easier access for securing the needle 3, for example. It may then be returned to the first state e.g. for dispense.

As the shape of the needle housing 10 suggests in FIG. 1A, the first flow direction is aligned parallel to the longitudinal axis X while the second flow direction is aligned perpendicular to the longitudinal axis X. As an advantage, the inlet section of the needle 20 may be connected to a fluid reservoir of the assembly retaining a fluid, wherein the needle is fluidly connected to the reservoir unless this is not explicitly indicated or described in FIG. 1B. The fluid reservoir, such as a cartridge may be housed by the first housing part 1a, for example.

The first housing part 1a is further provided with a dose indicator 8 which may comprise a window through which e.g. the number or amount of a previously set or dispensed dose of fluid, such as drug or medicinal product may be indicated.

The first housing part 1a is further provided with a dose member 9 which may be manipulated by the user during setting of a dose of drug. Preferably, during setting, the dose member 9 is rotated by the user with respect to the housing 1. During setting, the assembly 100 is, preferably, in the first state.

The provision of the dose indicator 8 and the dose member 9 is particularly expedient, as the device 200 may relate to a device, wherein doses of drug can be varied and/or set by the user. The device 200, preferably, further relates to a semiautomatic, or automatically driven drug delivery device.

The second housing part 1b comprises a shield 2 which is arranged to prevent or hinder the needle body 4 or a section thereof from being visible for a user of the assembly or the device, especially during administration or dispensing. It may also be advantageous for protecting the cartridge from damage or dirt during storage. The assembly 100 further comprises a drive mechanism (not explicitly indicated).

FIG. 10 shows the assembly 100 in a second, as-dispensed or closed state, wherein the first housing part 1a has already been moved or pressed towards the second housing part 1b such that said housing parts abut. The second state may additionally relate to a storage state of the assembly 100. A clip or manually operated lock (not explicitly indicated) may retain the assembly 100 in this second state for storage. In this state, the shield 2, preferably, completely visually shields the needle unit 5 or the needle hub 6.

During administering or dispensing of fluid, the first housing part 1a is pressed or moved with respect to the second housing part 1b by the user. Expediently, the assembly 100 is configured such that by said movement, fluid contained in the fluid reservoir can be administered through the needle 3. In order to be pressed against and relative to the second housing part 1b, the first housing part 1a further comprises an activation face 7 which the user can contact, e.g. manually. Consequently, a bung contained within an axially oriented cartridge for fluid reservoir may e.g. be moved, by a piston rod (not explicitly indicated). An axial movement of the piston rod expediently effects an administration or dispensing of fluid through the needle, when the first housing part 1a is moved (radially) with respect to the second housing part 1b. This may be facilitated by the mentioned drive mechanism which may comprise one or more further components of the device 200 which transfer a radial movement of the first housing part 1a with respect to the second housing part 1b into an axial movement of said components and/or the piston rod with respect to the second housing part 1b.

Figure 3:
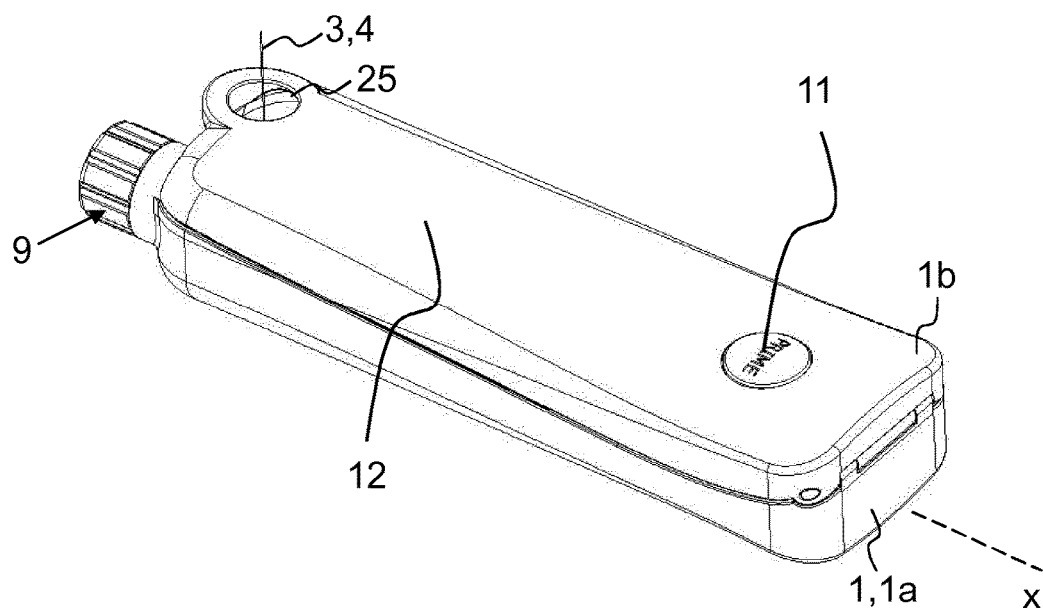
FIG. 3 shows a perspective view of the assembly being in the second state.

In FIG. 3, the device 200 is shown with a surface of the second housing part 1b facing upwards. The surface of the second housing part 1b comprises or defines a contact area 12 for contacting a surface into which the fluid is to be administered or dispensed. The second housing part 1b further comprises an opening 25, wherein the opening 25 is provided in the contact area 12. The opening is, preferably, arranged and configured such that the needle body 4 or the outlet section 21 of the needle body 4 may at least partly be moved through the opening 25, when the first and the second housing part 1b are moved relatively such that the outlet section 21 protrudes through the opening 25 from the housing 1. The drive mechanism and the assembly 100 or the device 200 are, preferably, configured such that, during relative movement of the first and the second housing part 1a, 1b, the outlet section 21 is firstly moved through the opening such that it protrudes a certain distance through the opening 25 of the second housing part 1b sufficient to pierce the skin of the user, and sequentially fluid is administered through the needle 3, particularly through the outlet section 21.

When at least one of the first and the second housing part 1a, 1b is released again by the user, said housing parts are (at least at the distal end 24) moved away from each other, e.g. by the biasing spring, and the dispensing operation is, expediently stopped or interrupted. In other words, the housing 1 is opened again, wherein also the outlet section 21 of the needle body 4 is moved through the opening 25 in a direction opposite to the one in which the outlet section 21 moved during dispensing, preferably such that it does no longer protrude through the opening 25 from the housing 1.

Figure 2A:
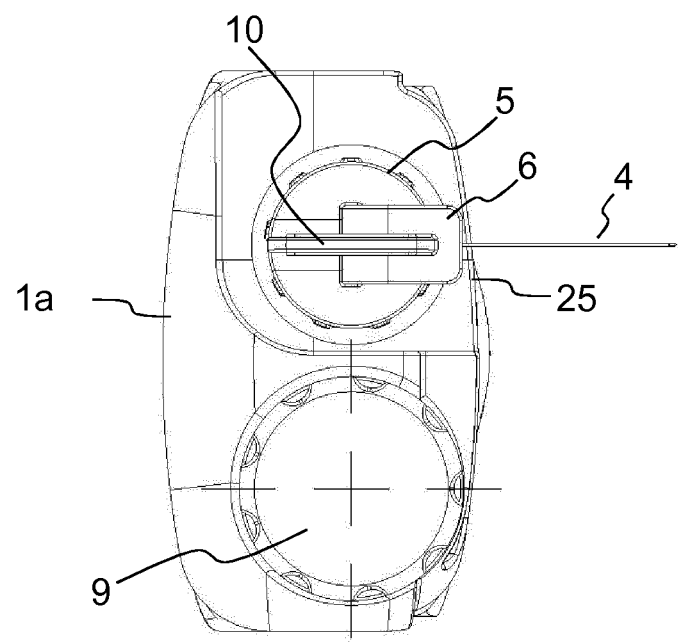
FIG. 2A shows a top view of parts of the assembly, wherein the needle hub is in an administration position.

FIG. 2A shows a top view of the first housing part 1a. Particularly, a distal end of parts of the assembly is shown. Although the second housing part is not shown in FIG. 2A, the first housing part 1a basically determines a contour or e.g. a cross-section of the device 200. In the top view of FIG. 2A, the needle unit 5 is shown located above the dose member 9. The needle hub 6 is arranged in or aligned according to an administration position in which the outlet section 21 is aligned perpendicular to the longitudinal axis X (not shown in FIG. 2A) of the housing 1, as is also the case in FIG. 1A for example. In the administration position, the outlet section 21 would also be aligned perpendicular to the contact area 12 of the second housing part 1b, if the second housing part was mounted to the first housing part 1a in FIG. 2A.

Figure 2B:
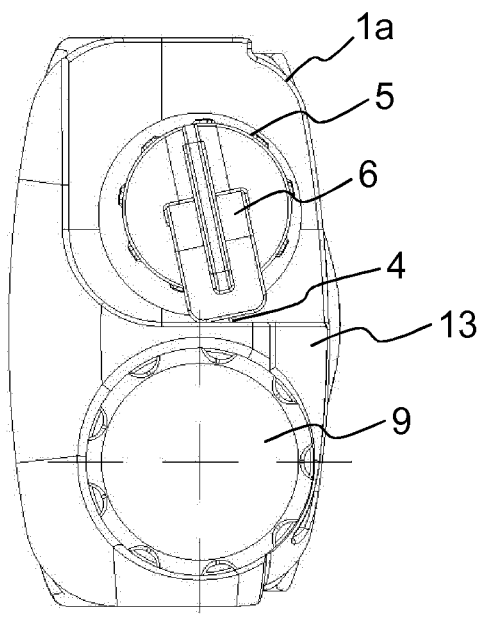
FIG. 2B shows a top view of parts of the assembly, wherein the needle is in a storage position.

FIG. 2B shows a situation in which, as compared to FIG. 2A, the needle hub 6 has been rotated from the administration position to a storage position. The first housing part 1a comprises a recess 13 (shown in top view only in FIG. 2B). With the needle hub 6 being in the storage position, the needle body is at least partly rotated under the recess 13 such that the needle body 4 is at least partly covered by the first housing part 1a and prevented or hindered from being visible for a user. Furthermore, the outlet section 21 points towards the dose member 9, wherein it is no longer accessible and the danger of needle stick injuries for the user can be prevented.

In FIG. 3, the device 200 is shown being provided with a priming button 11 located near the proximal end 23. The device 200 further comprises a priming mechanism (not explicitly indicated) in addition to or as part of the drive mechanism. The priming mechanism is expediently coupled to the priming button 11. The priming mechanism is configured such that one or more, such as two priming doses or safety shots, of fluid can be administrated by activating the priming mechanism when the assembly is in the second or closed state. The priming mechanism relates to a safety aspect, as the risk of needle stick injury is reduced when, during priming, the device is in the second state. Particularly, priming ensures that a bearing e.g. of or connected to a piston rod of the device or to another component thereof is in contact with a bung or piston. Thereby, e.g. fabrication tolerances between components of the drive mechanism can advantageously be compensated for. The safety shots ensure that the needle 3 is e.g. not blocked. The safety shot may further be performed after a new needle is fixed to the device.

As an alternative to the described embodiments, the drive mechanism and the needle unit may also be provided by the second housing part 1b.

The presented concept enables that an administration or dispensing operation can be carried out more discretely. The user is not directly involved in the dispensing process and the needle itself is less visible to the user during this process, which can make the device easier to use for users with a needle phobia. In addition, needle functions and movements with respect to the housing can make the administration more controllable, aiding users with limited manual dexterity.

Advantageously, the relative movement of the first and the second housing part 1a, 1b to trigger a dispensing requires relatively low user force, as the concept is, preferably, designed for an application in semiautomatic or automatically driven, e.g. spring-driven, drug delivery devices.

The scope of protection is not limited to the examples given herein above. The disclosure is embodied in each novel characteristic and each combination of characteristics, which particularly includes every combination of any features which are stated in the claims, even if this feature or this combination of features is not explicitly stated in the claims or in the examples.

REFERENCE NUMERALS

1 Housing
1a First housing part
1b Second housing part
2 Shield
3 Needle
4 Needle body
5 Needle unit
6 Needle hub
7 Activation face
8 Dose Indicator
9 Dose member
10 Needle housing
11 Priming button
12 Contact area
13 Recess
20 Inlet section
21 Outlet section
22 Bend
23 Proximal end
24 Distal end
25 Opening
100 Assembly
200 Drug delivery device
X Longitudinal axis

The invention claimed is:

1. An assembly comprising:
a needle for administering a fluid, the needle comprising:
 a hollow needle body configured to guide the fluid, the needle body being formed such that an inlet section of the needle body defines a first flow direction for the fluid, and an outlet section of the needle body defines a second flow direction for the fluid, wherein the first flow direction is inclined with respect to the second flow direction, and wherein the needle body comprises a bend which connects the inlet section and the outlet section;
a needle unit comprising the needle, the needle being fixed to a needle hub, wherein the needle unit further comprises a needle housing which covers a part of the bend of the needle body,
a reservoir retaining fluid, wherein the needle is fluidly connected to the reservoir, and
an assembly housing, wherein the needle unit is rotatably mounted to the assembly housing such that the needle hub is axially secured but rotatable with respect to the assembly housing, the needle unit being rotatable relative to the assembly housing such that a longitudinal axis of the outlet section of the needle body points toward a dose member.

2. The assembly according to claim 1, wherein the needle body is formed such that the first flow direction and the second flow direction are right-angled.

3. The assembly according to claim 1, wherein the needle hub is rotatable around the first flow direction.

4. The assembly according to claim 1, wherein the assembly housing comprises:
a first housing part; and
a second housing part, wherein the needle is secured to the first housing part,
wherein the assembly comprises a drive mechanism, and
wherein the assembly is configured such that the first housing part is movable in a first direction relative to the second housing part to activate the drive mechanism to dispense fluid through the needle.

5. The assembly according to claim 4, wherein the first housing part and the second housing part are pivotally connected to each other, and wherein the first housing part is spring-biased away from the second housing part or vice versa.

6. The assembly according to claim 4, wherein the second housing part comprises an opening, and
wherein the assembly is configured such that, by a movement of the first housing part with respect to the second housing part, the needle is at least partly movable through the opening such that the outlet section of the needle body protrudes through the opening from the assembly housing.

7. The assembly according to claim 6, wherein the first housing part retains the drive mechanism, and
wherein the assembly is configured such that, as soon as the outlet section protrudes a certain distance through the opening during movement of the first housing part with respect to the second housing part, fluid is administered through the needle.

8. The assembly according to claim 6, wherein the second housing part comprises a contact area for contacting a surface into which the fluid is to be administered, and wherein the opening is provided in the region of the contact area.

9. The assembly according to claim 4, wherein the second housing part comprises a shield configured to prevent or hinder the outlet section of the needle from being visible for a user.

10. The assembly according to claim 4, wherein the assembly is configured such that the first housing part is movable in a second direction, relative to the second housing part to deactivate the drive mechanism to stop dispense of fluid through the needle, wherein the second direction is opposite the first direction.

11. The assembly according to claim 1, wherein the needle is rotatable from an administration position to a storage position, and
wherein the assembly is configured such that, when the needle is in the storage position, the needle is prevented from being visible for a user.

12. The assembly according to claim 1, wherein the fluid comprises a pharmaceutically active compound.

13. An assembly comprising:
a needle with an inlet, an outlet, and a hollow body that connects the inlet and the outlet, wherein the body has a bend,
a needle hub, wherein the needle is fixed to the needle hub,
a reservoir containing fluid, the reservoir is in fluid communication with the needle, and
a housing,
wherein the inlet of the needle defines a first flow direction for the fluid and the outlet of the needle defines a second flow direction for the fluid, wherein the first flow direction is inclined with respect to the second flow direction, and
wherein the needle hub is rotatably mounted to the housing such that the needle hub is axially secured but rotatable with respect to the housing, the needle hub being rotatable relative to the housing such that a longitudinal axis of the outlet of the needle points toward a dose member.

14. An assembly comprising:
a needle with an inlet, an outlet, and a hollow body that connects the inlet and the outlet, wherein the body has a bend, a needle hub, wherein the needle is fixed to the needle hub, a reservoir containing fluid, wherein the reservoir is in fluid communication with the needle, an assembly housing comprising a first housing part and a second housing part, and a needle housing for supporting the needle, wherein the inlet of the needle defines a first flow direction for the fluid and the outlet of the needle defines a second flow direction for the fluid, wherein the first flow direction is inclined with respect to the second flow direction, and wherein the needle hub is rotatably mounted to the first housing part such that the needle hub is axially secured but rotatable with respect to the first housing part, the needle hub being rotatable relative to the assembly housing such that a longitudinal axis of the outlet of the needle points toward a dose member.

* * * * *